(12) United States Patent
Knierim

(10) Patent No.: US 12,736,166 B2
(45) Date of Patent: Sep. 15, 2026

(54) CENTERING INTERFACE

(71) Applicant: B. Braun Avitum AG, Melsungen (DE)

(72) Inventor: Michael Knierim, Bad Sooden-Allendorf (DE)

(73) Assignee: Braun Avitum AG, Melsungen (DE)

( * ) Notice: Subject to any disclaimer, the term of this patent is extended or adjusted under 35 U.S.C. 154(b) by 0 days.

(21) Appl. No.: 18/954,305

(22) Filed: Nov. 20, 2024

(65) Prior Publication Data

US 2025/0164052 A1 May 22, 2025

(30) Foreign Application Priority Data

Nov. 21, 2023 (DE) ..................... 10 2023 132 347.4

(51) Int. Cl.
*F16L 37/50* (2006.01)
*A61M 1/14* (2006.01)
*F16L 33/28* (2006.01)

(52) U.S. Cl.
CPC ............... *F16L 37/50* (2013.01); *A61M 1/14* (2013.01); *F16L 33/28* (2013.01); *A61M 2209/086* (2013.01)

(58) Field of Classification Search
CPC ......... F16L 27/02; F16L 27/10; F16L 27/026; F16L 27/08; F16L 37/52; F16L 37/50;
(Continued)

(56) References Cited

U.S. PATENT DOCUMENTS 5,603,531 A * 2/1997 Maier .................. F16L 27/026 285/145.1
6,036,858 A * 3/2000 Carlsson ............ A61M 1/1668 604/4.01
(Continued)

FOREIGN PATENT DOCUMENTS

CH 670955 A 7/1989
DE 102012023392 A1 6/2014
(Continued)

OTHER PUBLICATIONS

Search Report received in European Application No. 24214042.4-1113 dated Mar. 28, 2025, with translation, 13 pages.
(Continued)

*Primary Examiner* — David Bochna
(74) *Attorney, Agent, or Firm* — Christopher A. Rother; CM Law

(57) ABSTRACT

A centering interface is arranged between a tubular element mounted in a device, specifically a receiving tube or quiver, for a suction rod of a dialysis machine, and a movable element preferably guided pivotally about an axis, specifically a front plate of the dialysis machine. Centering surfaces are mated between the tubular element mounted in the device and the movable element. When a preferably sealed joint of the interface is manufactured, the tubular element mounted in the device can be moved in the axial direction against the force of a biasing spring during the movement of the movable element and the accompanying approach of the centering surfaces, while its guiding support allows a movement that permits the centering surfaces to be brought into the joining position with centering surface axes aligned with each other free of constraint forces.

16 Claims, 7 Drawing Sheets

(58) Field of Classification Search
CPC .... A61M 1/1668; A61M 1/152; A61M 1/156; A61M 1/14; A61M 2209/086; A61M 2209/084; H05K 7/20781; H05K 7/20818; H05K 7/20772; H05K 7/20272
USPC ...................................... 285/63, 302; 604/29
See application file for complete search history.

(56) References Cited

U.S. PATENT DOCUMENTS

| | | | | |
|---|---|---|---|---|
| 7,223,262 | B2 * | 5/2007 | Brehm | A61M 1/1668 604/905 |
| 7,736,328 | B2 * | 6/2010 | Childers | A61M 1/1668 604/905 |
| 8,460,544 | B2 * | 6/2013 | Volker | A61M 1/1668 210/321.71 |
| 8,580,112 | B2 * | 11/2013 | Updyke | A61M 1/3472 604/93.01 |
| 10,471,188 | B1 * | 11/2019 | Zollinger | A61M 1/79 |
| 2009/0009290 | A1 * | 1/2009 | Kneip | A61M 1/152 340/10.1 |
| 2012/0289765 | A1 * | 11/2012 | Kaushansky | A61M 60/495 600/18 |
| 2013/0245531 | A1 * | 9/2013 | Brandl | A61M 1/1668 604/4.01 |
| 2015/0000758 | A1 * | 1/2015 | Randall | A61M 1/168 137/15.01 |
| 2015/0021255 | A1 | 1/2015 | Takahashi et al. | |
| 2017/0209635 | A1 * | 7/2017 | Paraluppi | A61M 1/1656 |
| 2017/0304519 | A1 * | 10/2017 | Jonas | A61M 1/1668 |
| 2019/0054225 | A1 * | 2/2019 | Nimura | A61M 1/1668 |
| 2019/0167870 | A1 * | 6/2019 | Korkeamäki | A61M 1/84 |
| 2020/0268957 | A1 * | 8/2020 | Schmitt | A61M 1/1668 |
| 2022/0133424 | A1 * | 5/2022 | Liang | A61M 1/63 141/231 |
| 2023/0110189 | A1 | 4/2023 | Irrgang | |
| 2023/0246367 | A1 | 8/2023 | Gloessl et al. | |
| 2023/0320932 | A1 * | 10/2023 | Brehm | A61M 1/1668 604/5.01 |

FOREIGN PATENT DOCUMENTS

| | | | |
|---|---|---|---|
| DE | 102020104101 | A1 | 8/2021 |
| WO | 2022032313 | A1 | 2/2022 |

OTHER PUBLICATIONS

Search Report received in German Application No. 10 2023 132 347.4 dated Aug. 12, 2024, with translation, 14 pages.

* cited by examiner

A26=A50
50
30
24
42
52
34
A34=A42
34B
54

52
A42=A50
56

30
26
A26
32
50

A34
42

134A
134B
140
142
156
A134
134
144
148

138
156
134
134
140

130
170
150
124
A134

CENTERING INTERFACE

CROSS-REFERENCE TO RELATED APPLICATION(S)

This application claims priority under 35 U.S.C. § 119 to German Application No. 10 2023 132 347.4, filed on Nov. 21, 2023, the content of which is incorporated by reference herein in its entirety.

FIELD

The invention relates to a centering interface between a fixture-mounted tubular element, specifically a receiving tube (quiver) for a suction rod of a dialysis machine, and a movable element guided pivotally about an axis, specifically a front plate of a dialysis machine.

BACKGROUND

Interfaces of this type are required, for example, in medical devices such as dialysis machines to provide a clean interface for a suction rod by which bicarbonate and/or concentrate from canisters usually positioned on a base can be taken. For this purpose, so called quivers for receiving suction rods not in use or stored for the rinsing operation are usually provided on the dialysis machine.

There are known relevant interfaces in which, for example, two vertically superimposed quivers are located in the dialysis machine, while dimensionally accurate breakthroughs are formed in a pivotable front plate of the dialysis machine for receiving the front ends of the quivers. The tolerance chain makes it difficult, however, even with manual adjustment which involves considerable time for assembly, to achieve a clean interface. The result is a visible gap undesired by the user through which liquid can enter into the machine and cleaning is difficult.

In order to prevent undesired gaps from forming, in other known machines the quiver is designed as a single fixed assembly group which has no more movable component parts.

Since meanwhile the users expect all ports and interfaces to be provided on the movable front plate in an easily accessible and ergonomically optimized manner, and as usually there remains no more space for a fixed quiver group beneath the front plate, because there canisters for concentrate and the like are positioned, there is a need to provide an interface of the above-described type that allows to seal the quiver mounted in the dialysis machine in a clean and gap-free manner when closing the front plate without complicated mounting and adjusting steps being required.

SUMMARY

In accordance with the invention, the quiver can still be mounted separately from the movable element of the interface, i.e. from the front plate of a dialysis machine. Thus, complicated integration of a fixed element into the front plate which would entail many positions that are difficult to clean because of the required sealings can be omitted. Furthermore, a centering surface, such as a conical surface mating or ball/spherical cap surface mating, is provided between a quiver mounted in the device and the front plate, with the advantage that a centering large-area arrangement of the interface elements can be achieved via said surfaces. The arrangement is further made in such a way that, when manufacturing a preferably sealed joint of the interface, during movement of the front plate, such as a swivel movement, and the accompanying approach of the centering surfaces with only slowly aligning axes, the quiver can be moved in the axial direction against the force of a biasing spring, while its guiding support in the device allows a movement which permits the centering surfaces to be brought into a joining position with centering surface axes being aligned with each other free of constraint forces. Due to the spring-loaded element which also allows an initial angular offset during the movement pattern such as the pivoting of the front plate, the components/parts to be joined are positioned appropriately in the interface, with any tolerances being compensated. Thus, the interface is joined solely by the movement of the front plate. Time-consuming adjustments at the interface can be dispensed with.

Moreover, there is the additional advantage that the interface can be positioned at any position at the front face of the device and that, when plural interfaces are formed, the position allocation of said interfaces relative to each other can be freely selected. In this way, for example two rinse chambers (quivers) can be juxtaposed to save vertical space.

It turns out that it is possible to ensure, by means of a simple plain bearing for the quiver mounted in the device, clean and permanently lasting positioning of the quiver, in particular because the axial movement of the quiver occurring when joining the interface is within the range of millimeters.

The degree of freedom of the support required when joining the interface to compensate the angular offset of the centering surfaces can be realized in various ways. A simple device variant advantageously consists in designing the plain bearing in a bearing block that is movable within the device at least in a plane which is perpendicular to an axis of movement of the front plate. It is sufficient for the required lateral mobility to provide a fastening of the bearing block with slight play in the device.

When the plain bearing is fixed in a bearing block via a spherical cap, an extended freedom of movement is imparted to the tubular element of the quiver while at the same time an exact axial guide is maintained. Supports in which a plain bearing is fixed in a bearing block via a spherical cap are available as component parts, for example as so-called pedestal bearings which are sold under the registered trademark IGUBAL® with spherical cap sold under the registered trademark IGLIDUR® W300.

A particularly simple support in terms of device technology of the quiver is provided when the plain bearing has a slightly conical bearing surface that tapers toward the front end of the quiver. The conical angle can be within the low single-digit degree range. This design offers the additional advantage that, when the bearing sleeve is an injection-molded part, the conical angle is desired as draft angle anyway.

When the biasing spring bears against the bearing block, the pressure spring can be designed to have a relatively large length, thus allowing the spring characteristic to be determined more accurately and to be positioned in ranges optimal as regards the contact forces occurring.

It is basically possible to form the external centering surfaces either on the quiver or on the front plate. In terms of manufacture, it is more reasonable, however, when an outer centering surface which can be brought into centering joint fit engagement with an inner centering surface in the front plate is formed on the end face of the element mounted in the device.

When, on the quiver, the outer conical surface is adjacent to a radial collar in which an annular seal for abutment on an inner wall of the front plate is accommodated, a safe liquid sealing against the interior of the device results when joining the interface. Accordingly, by appropriately selecting the annular seal, it can be easily ensured that the elastic deformation of the annular seal admits a complete contact of the centering surfaces so that any formation of gaps is avoided when the interface is joined.

Another simplification of the design of the front end of the quiver results from the variant according to which a peripheral flute for receiving the seal ring is formed in the outer centering surface.

When the axis of the quiver of a dialysis machine is inclined relative to a horizontal plane from the interface downwards at an angle that is e.g. between 20° and 30°, the openings of the quiver are more easily accessible for the operator of the dialysis machine, in particular when the interface is arranged at the lower end of a front plate of the dialysis machine. It has shown that the configuration according to the invention allows even angles of inclination up to 60°, preferably up to 45°, particularly preferred up to 30°, to be easily realized.

The user friendliness is equally improved when the centering surface in the front plate has an axis that is inclined by an angle of attack of several degrees relative to a plane perpendicular to the axis of movement of the front plate. In this way, the above-described angle of inclination of the quiver axis can be increased more easily.

The interface is facilitated in terms of manufacture when the mating of the centering surfaces is formed by a mating of conical surfaces.

A particularly advantageous field of application of the interface is constituted by a device for extracorporeal blood treatment, specifically a dialysis machine, comprising at least one interface as described above. Accordingly, the movable element of the interface is a front plate attached to a rack via a hinge connection which preferably accommodates an insert in which the centering or conical surface is formed.

The interface offers the particular advantage that it can be designed equally for plural preferably horizontally or vertically adjacent accesses to the device, that is for plural sockets of suction tubes of a dialysis machine, for example. Consequently, there can be provided identically designed interfaces, although in this case the movement curves of the centering surfaces on the movable element have different radii due to the different distance from the hinge axis of the front plate. The accesses need not be horizontally adjacent, they can also be vertically superimposed when the front plate has a hinge joint with a horizontal axis.

In this case, it is even possible to assign a shared or common bearing block to the adjacently mounted tubular elements, thus allowing the design to be further facilitated.

BRIEF DESCRIPTION OF THE DRAWINGS

In the following, embodiments of the invention are illustrated in detail on the basis of schematic drawings, wherein.

DETAILED DESCRIPTION

Figure 1:
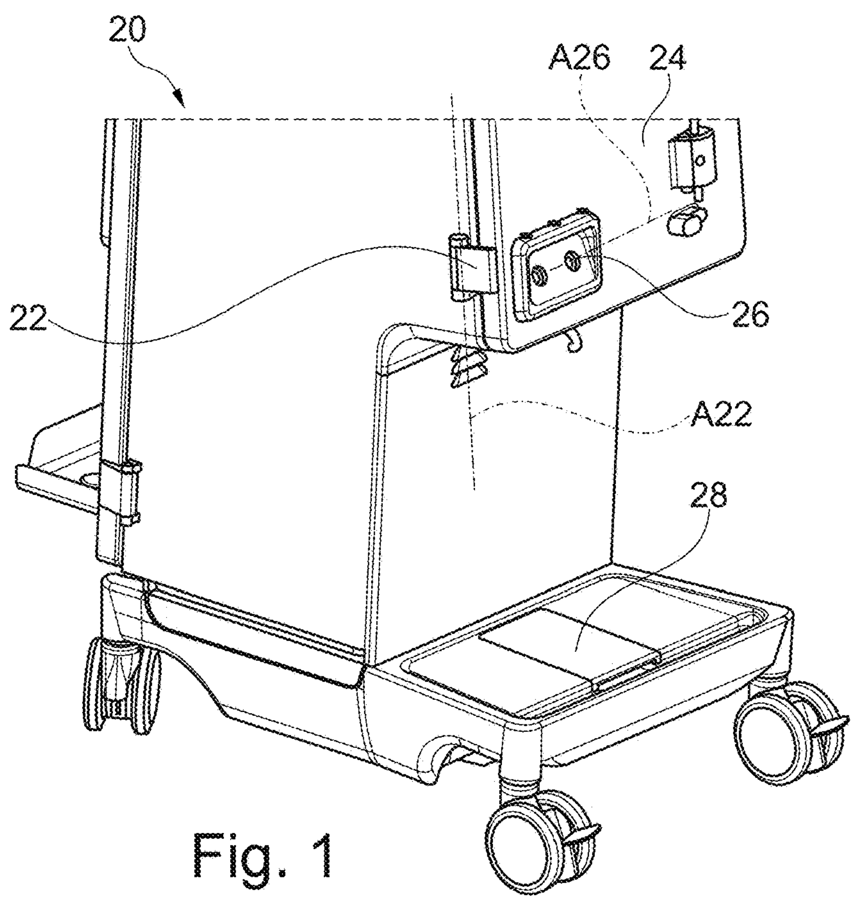
FIG. 1 shows a perspective partial view of a dialysis machine having an access for two suction rods to a quiver.
Figure 3:
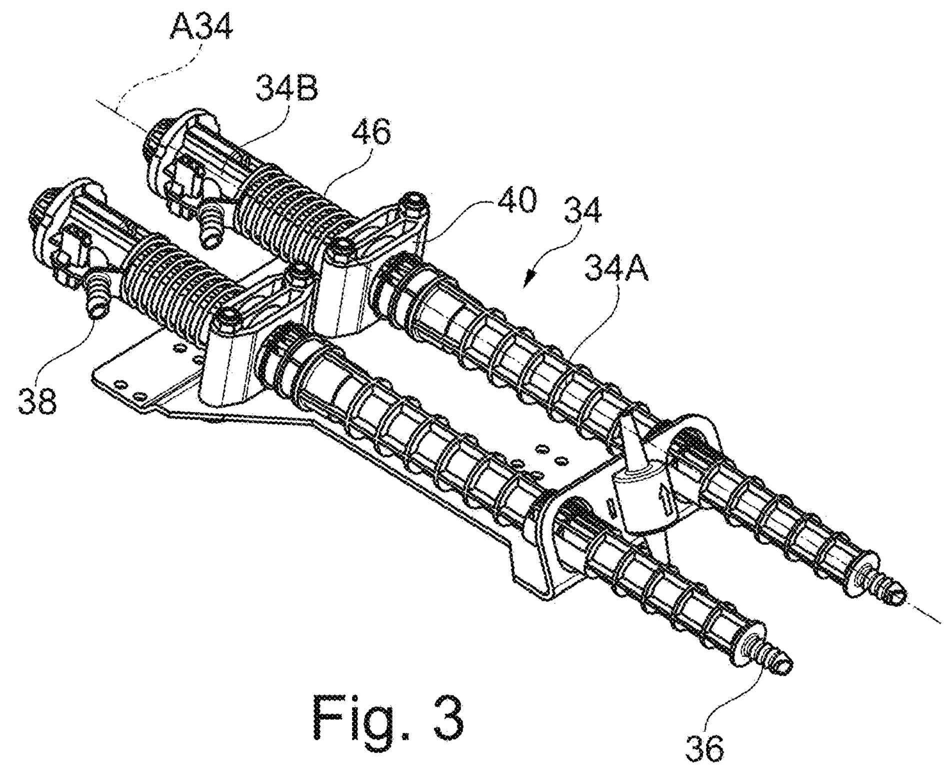
FIG. 3 shows a perspective view of two horizontally adjacent quivers of the dialysis machine.

In FIG. 1, reference numeral 20 designates a dialysis machine to which a front plate 24 is hinged via a hinge connection 22 with the hinge axis A22. In the front plate 24 of a dialysis machine, as a rule the most diverse units and sockets are integrated, such as peristaltic pumps, infusers and the like, as well as accesses 26 to so-called quivers—shown in FIG. 3—into which e.g. suction rods can be inserted which are connected, via hoses, to canisters (not shown) which are positioned, for example, on a bottom plate/base 28 of the dialysis machine 20 beneath the front plate 24. The quivers 34 in the shown embodiment are identical, but they can also have different dimensions.

Figure 2:
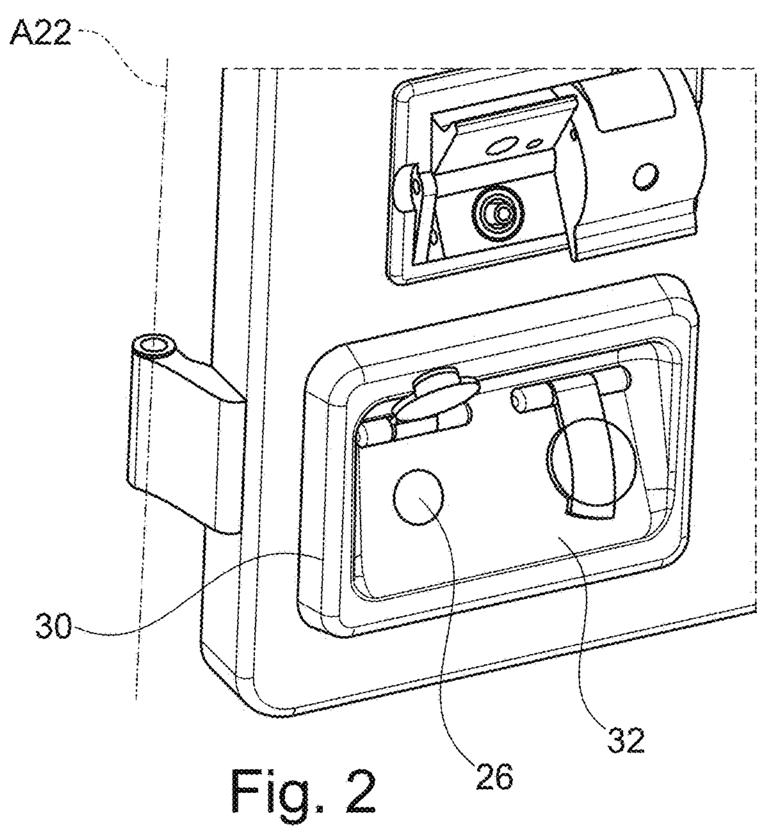
FIG. 2 shows the detail II of FIG. 1 in an enlarged scale.

The accesses 26 are shown enlarged in FIG. 2. They are located in an insert 30 that is shown in an enlarged view in FIG. 5 and includes an insert wall 32 inclined by several degrees relative to the front plate 24 so that the accesses 26 are more easily accessible for the operator of the dialysis machine and can be seen better from above. The axes of the axes of the accesses 26 which are usually perpendicular to the insert wall 32 are designated with A26—as can be seen best from FIG. 5 —.

Figure 4:
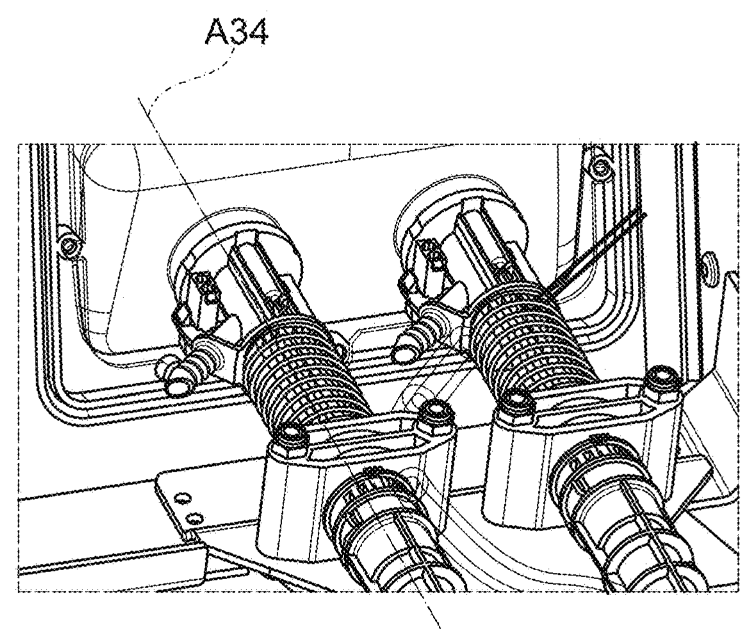
FIG. 4 shows an enlarged perspective view of the quivers shown in FIG. 3 in interaction with an insert in a front plate of the dialysis machine.

When the front door 24 is closed, the accesses 26 are located—as shown in FIG. 4—to be axially and radially aligned and sealed in front of the quivers 34 which have an axis A34 and usually are mounted in the dialysis machine 20 in such a way that the axis A34 is inclined relative to a horizontal plane by a particular small angle that can be designed up to ranges of 60°, preferably 45°, and is between 20° and 30°, for example. For this purpose, a centering interface is provided between the quiver 34 and the front plate 24, which will be described in greater detail hereinafter, which allows to seal the quiver 34 mounted in the dialysis machine 20 in a clean and gap-free manner when closing the front plate 24, without complicated assembly and adjustment being required.

Figures 5, 6, 7A, 7B:
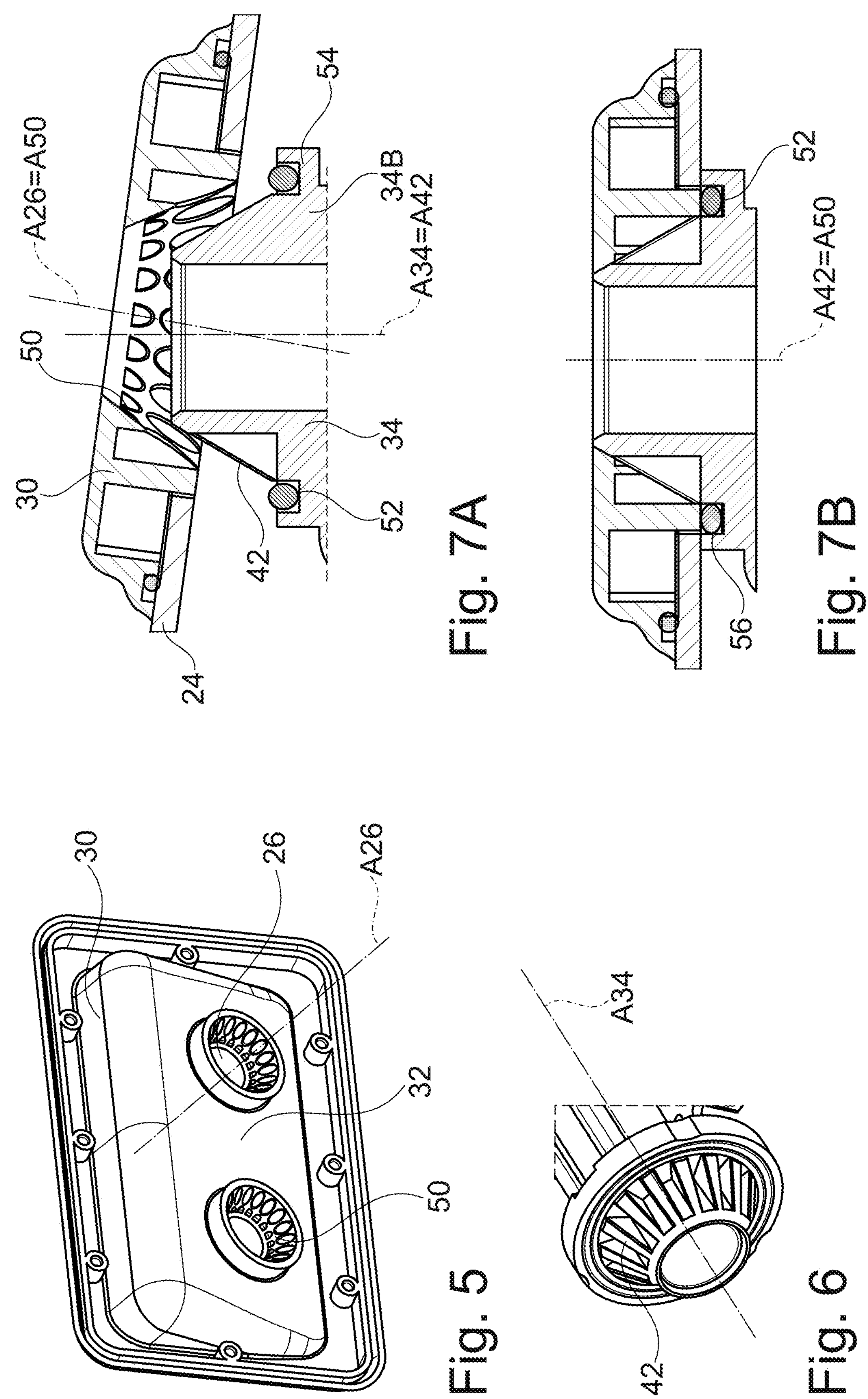
FIG. 5 shows an enlarged representation of a perspective view of the insert in the front plate shown in FIG. 4.
FIG. 6 shows a perspective view of the end face of the axially movably guided tubular element of the interface.
FIGS. 7A and 7B show schematic section views of the front plate and the quiver at different times of the joining operation of the interface between the quiver and the front plate.

The quivers 34 include a tubular inner component part 34A installed in the dialysis machine 20 comprising a feed port 36, such as for disinfectant, and an outer tubular component part 34B coaxial to the former that is equipped with discharge ports 38 and—see FIG. 6—a centering joining surface 42 on the end face. In the shown embodiment, the joining surface 42 referred to as quiver-side centering surface in the following is formed by a conical surface which is broken several times over the circumference so that the axis A42 of the centering surface 42 coincides with the axis A34. The quiver 34 is guided in a bearing block 40 to be movable in an axially limited manner, the bearing block forming a plain bearing for the quiver 34. More precisely, the quiver 34 is accommodated in a cylindrical bearing bore 44 (see FIG. 10) of the bearing block 40 against which a biasing spring 46 bears which presses the quiver 34 and, thus, the tubular component part 34B toward the front plate 24.

Figure 8B:
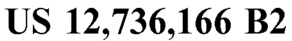
FIGS. 8A and 8B show perspective views of the guiding support of the tubular element when the front door of the dialysis machine is opened and closed.
Figure 8B:
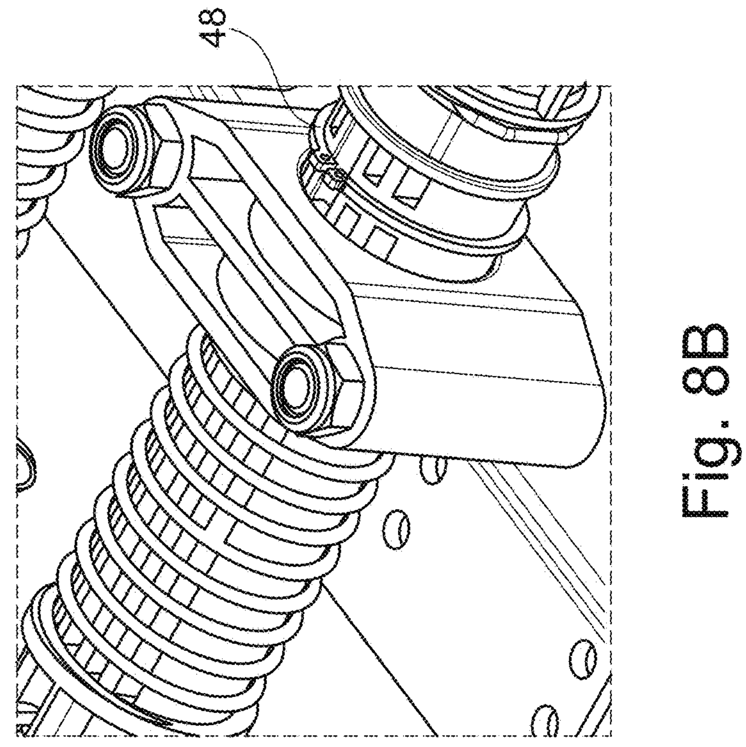
Figure 8A:
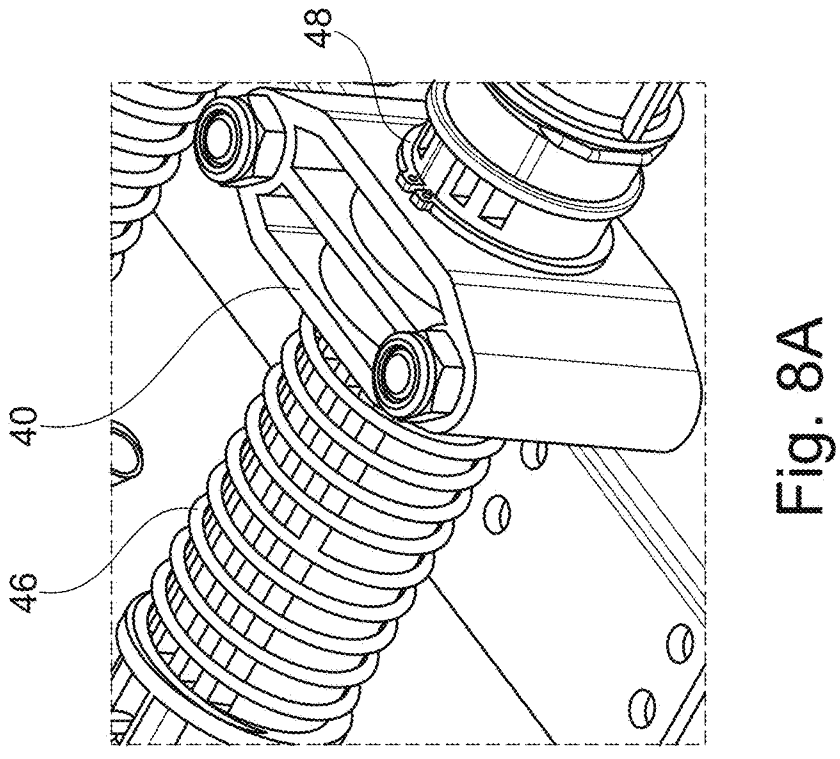

When the interface is not joined and, thus, the front plate 24 is opened, the biasing spring 46 presses the quiver 34 into the abutment position shown in FIG. 8A in which an axial retaining ring 48 abuts on the bearing block 40.

As a counter-piece to the first centering surface 42 on the quiver 34, in the insert wall 32 a front door-side centering surface 50 in the configuration of a conical surface with an axis A50 coinciding with the axis A26 is designed so that the centering surfaces 42 and 50 form a mating of centering surfaces which, when the front plate 24 is closed, ensures that the opening of the quiver 34 is sealed when positioned in the front plate 24. For this purpose, the following arrangement is made:

Due to the movable attachment of the front plate 24 on the dialysis machine 20, the centering surface 50 describes a movement of circular segment in the insert wall 32 so that the axis A26 of the centering surface 50 is not aligned with the axis A34 of the centering surface 42 on the quiver 34 at the beginning of the closing movement of the front plate 24. This state is schematically shown in FIG. 7A.

With the further progress of the closing operation, the centering surfaces 42, 50 increasingly approach each other so that the axes A26 and A34 are gradually in alignment with each other. Due to the initial eccentric contact of the centering surfaces 42 and 50, the component part 34B of the quiver 34 is axially displaced against the force of the biasing spring 46. At the same time, the arrangement is made so that the support guiding the component part 34B allows a compensation movement which permits the centering surfaces 42, 50 to be brought into the joining position shown in FIG. 7B with aligned centering surface axes A42 and A50 free of constraint forces. In said joining position, the centering surfaces 42, 50 configured as conical surfaces are fully adjacent to each other so that complete centering of the interface is given. In this position shown in FIG. 8B in which the axial retaining ring 48 is lifted off the bearing block 40, a seal ring 56 received in an annular groove 52 of a radial collar 54 is elastically deformed by the front plate 24, more precisely by the insert 30 located in the front plate 24 (see FIG. 7B), thus causing the access 26 of the socket to be sealed in a fluid-tight manner.

The axes A26 and A34 can be aligned in a simplified manner when the centering surface 50 in the front plate 24 has an axis A50 which is inclined downwards relative to a plane perpendicular to the hinge axis A22 of the front plate 24 by a predetermined angle with the dialysis machine 20.

Figure 10:
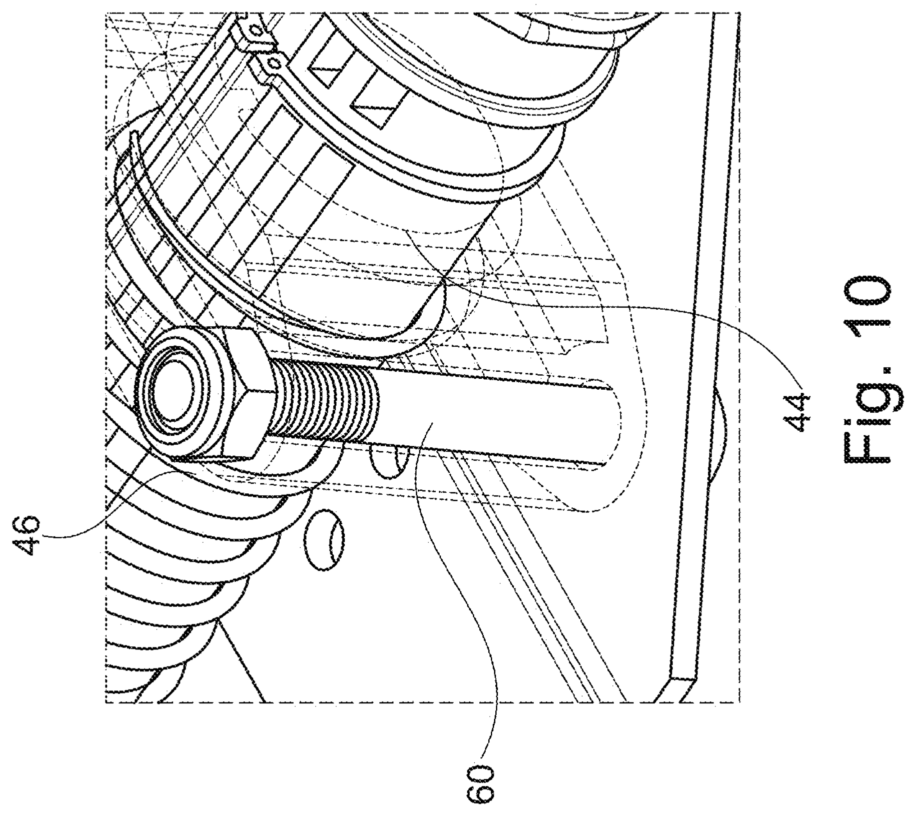
FIG. 10 shows a perspective partially transparent view of one side of a bearing block for the support according to FIG. 9.
Figure 9:
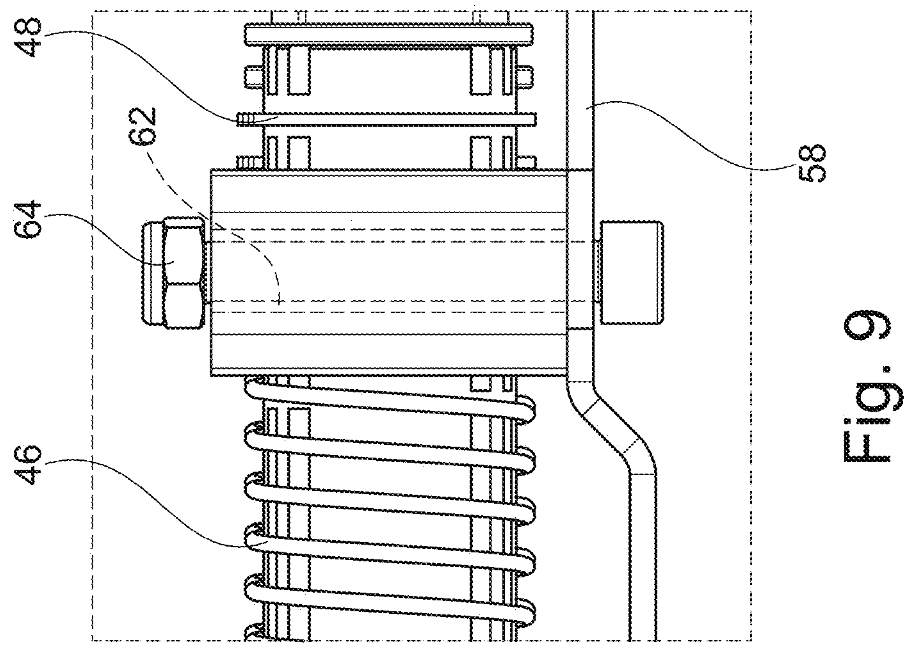
FIG. 9 shows an enlarged representation of the lateral or side view of the support for the tubular element.

Since the guided support of the component part 34B of the quiver 34 is a cylindrical plain bearing, and because the movement of the front plate 24 follows a circular movement curve during the closing operation, the bearing block 40 is mounted in the dialysis machine 20 as follows:

FIGS. 9 and 10 reveal that the bearing block 40 is mounted on a plate 58 which is located in a plane that is perpendicular to the axis A22 of the hinges 22 of the front plate 24. This is tantamount to the fact that fastening bolts designated with 60 of the bearing block 40 extend in parallel to the hinge axis A22. So that the angular offset and/or the misalignment can be compensated when closing and opening the front plate, a predetermined play in the screw connection of the bearing block 40 is utilized. To this end, the diameter of the bores 62 provided to receive the fastening bolts 60 in the bearing block 40 (see FIG. 9) is manufactured to be larger by a predetermined allowance than the bolt diameter. A self-locking nut 64 is slightly loosened after initial tightening for screwing the bearing block 40, which provides the bearing block 40 with the required movement play to compensate the above-described angular offset.

Figure 12:
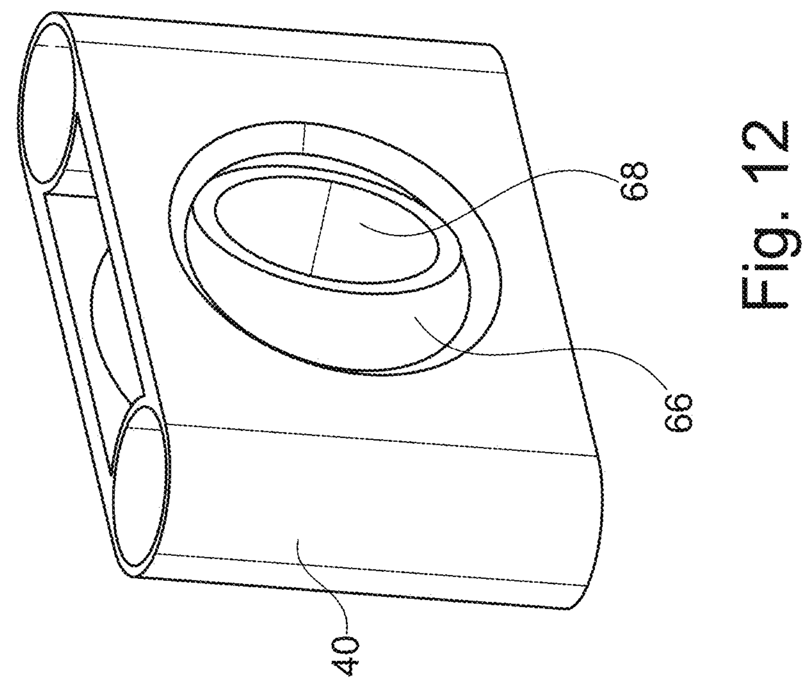
FIG. 12 shows a perspective view of the bearing block shown in FIG. 11.
Figure 11:
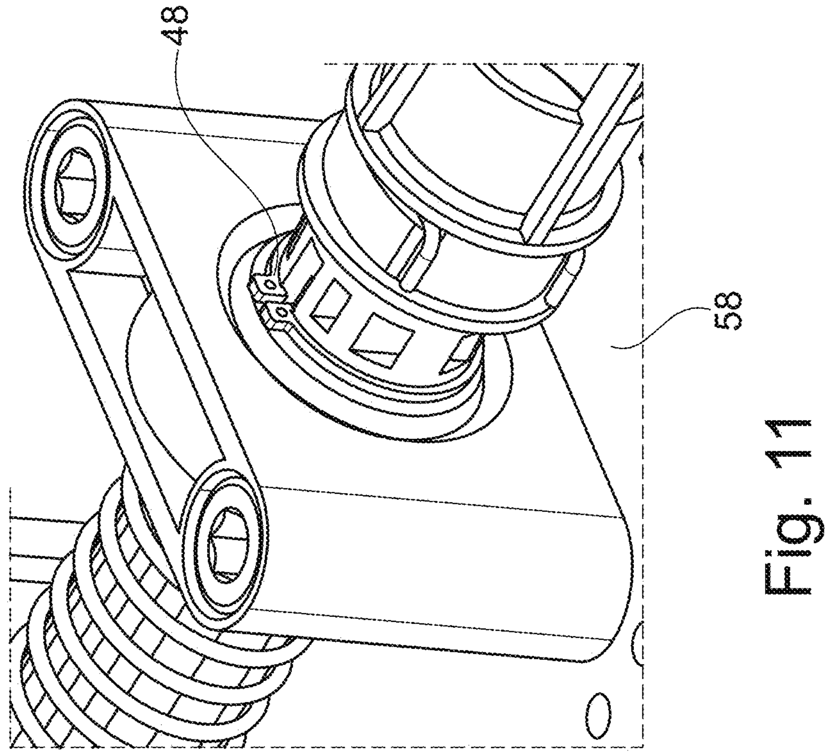
FIG. 11 shows a perspective view similar to FIG. 8 of a variant of the support for the tubular element.

In the above-described embodiment, the component part 34B is guided in a cylindrical plain bearing which is allowed to perform a linear displacement. Based on the FIGS. 11 and 12, a modified way of guiding the component part 34B is described.

The bearing block 40 tightly screwed on the plate 58 in this variant receives a plain bearing member 66 in the configuration of a spherical cap that has a cylindrical bearing bore 68 for receiving the component part 34B of the quiver 34. Those bearings are available on the market as so-called pedestal bearings and are sold, for example, by IGUS GmbH under the registered trademark IGUBAL® with spherical cap sold under the registered trademark IGLIDUR® W300. This type of support imparts additional freedom of movement to the quiver 34 with respect to the alignment of the axis A34 of the quiver 34 so that it is no longer required, when closing the front plate 24, to arrange the plate 58 perpendicularly to the hinge axis A22 for compensating the angular offset of the axes A34 and A26. Thus, there is more room for the inclination of the axis of the quiver 34 in the dialysis machine 20.

Hereinafter, based on the FIGS. 13 to 15, another modified embodiment of the interface will be described. Components of said variant which correspond to particular component parts of the afore-described embodiments are provided with corresponding reference numerals which are preceded by “1”.

Figures 13, 14, 15:
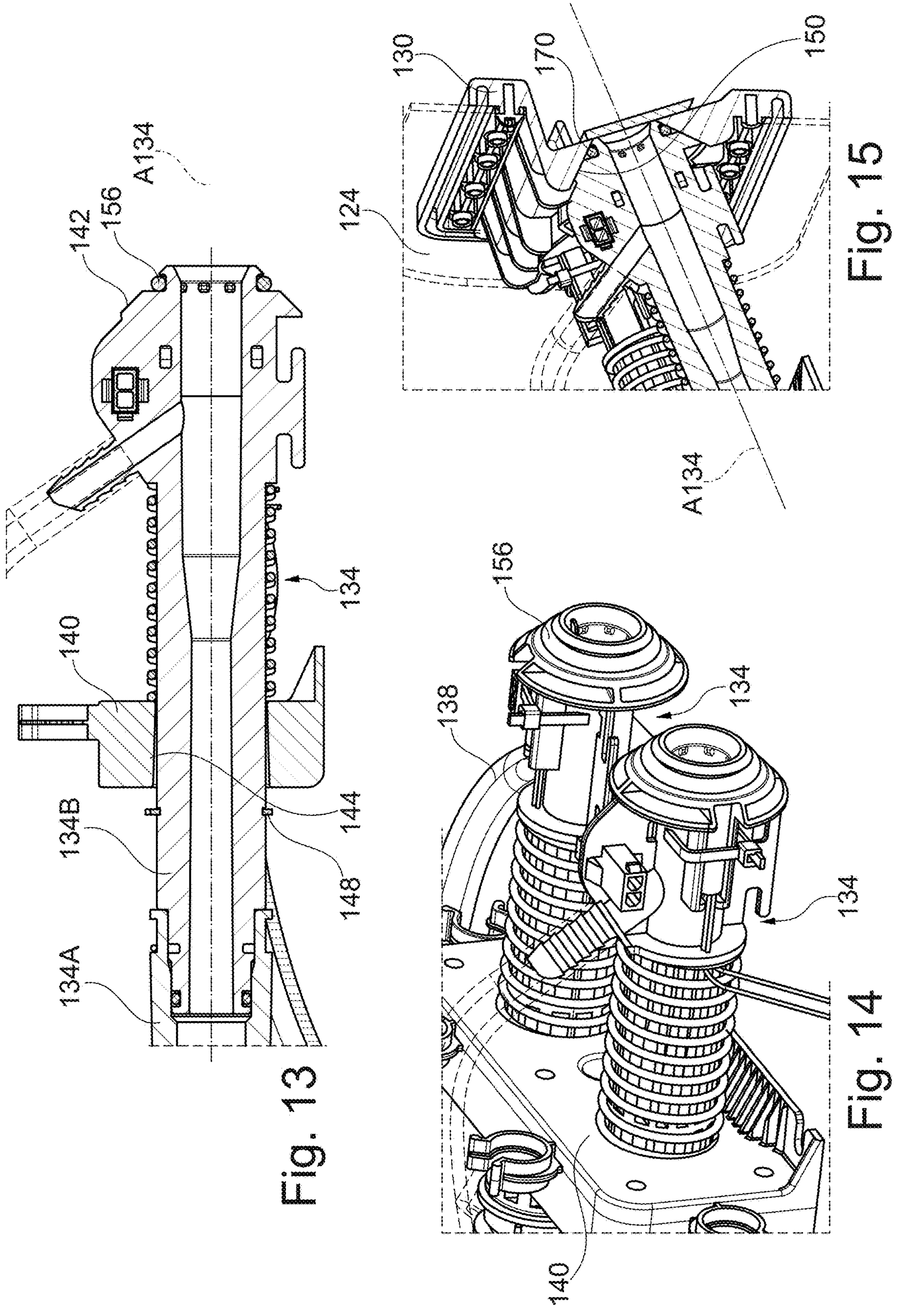
FIG. 13 shows a section view of a modified embodiment of the quiver being supported in the dialysis machine.
FIG. 14 shows a perspective view of two quivers mounted adjacently side by side in the dialysis machine in the configuration according to FIG. 13.
FIG. 15 shows, in a slightly enlarged scale, the perspective section view of the interface formed by the front plate and the quiver according to FIGS. 13 and/or 14 when joined.

One can see from FIG. 14 that two horizontally adjacent quivers 134 are supported to be guided in a shared bearing block 140.

The quiver denoted with 134 is structured—as shown by the longitudinal section across the quiver 134 according to FIG. 13—so that a front component part 134B which on the end face again forms a conical centering surface 142 that is broken several times over the circumference is accommodated to be slidingly movable in a component part 134A fixedly mounted in the dialysis machine 20. The complementary conical centering surface in the insert 130 that is located in the front plate 124 is denoted with the reference numeral 150. Deviating from the embodiment of the FIGS. 1 to 12, the guided support of the component part 134B is designed in the bearing block 140 so that it is formed by a slightly conical bearing surface 144. Said bearing surface may have a conical angle of a few angular degrees and it can extend in any direction.

In the shown embodiment, the conical bearing surface extends toward the component part 134A mounted in the device. This design of the support of the quiver 134 provides the latter with the required degree of freedom of movement when the front plate 24 is closed so that the centering surfaces 142, 150 can be brought into the joining position shown in FIG. 15 having conical surface axes aligned with each other free of constraint forces, while the component part 134B of the quiver 134 is displaced inwardly, i.e. toward the bearing block 140, against the force of the biasing spring 146. The admissible inclination of the longitudinal axis A134 of the quiver 134 can be influenced by selecting the conical angle of the bearing surface 144. In this way, for example the axis A134 of the quiver 134 can be inclined toward a horizontal plane by an angle that is in the range between 20° and 30°.

In further deviation from the above-described embodiment, the seal ring designated with the reference numeral 156 is received in a peripheral flute 170 which is formed in the centering surface 142 of the component part 134B designed as an outer cone. In the joining position of the interface shown in FIG. 15, the seal ring 156 is elastically compressed so far that the centering surfaces 142, 150 of the mating of centering surfaces fully abut against each other so that their respective axes coincide.

As a matter of course, deviations from the described embodiment are possible without leaving the basic idea of the invention.

The number and the relative position of the interfaces can be varied freely without having to modify the basic principle of adjustment-free sealing.

In the foregoing, the centering surfaces were described as conical surfaces. However, they can also be constituted by spherical segment surfaces and segment cap surfaces, etc.

The embodiments show a structure in which the convex centering surface is designed at the quiver, while the concave centering surface is provided in the insert of the front plate. This arrangement can also be reversed, however.

Also, the movement of the front plate is not limited to a pivoting movement about a hinge axis. The interface can also be used in other movement patterns of the movable element such as the front plate of a dialysis machine.

Consequently, the invention provides a centering interface between a tubular element mounted in a device, specifically a receiving tube (quiver) for a suction rod of a dialysis machine, and a movable element which is pivotally guided about an axis, for example, specifically a front plate of the dialysis machine. A mating of conical surfaces is provided between the element mounted in the device and the movable element and, when manufacturing a preferably sealed joint of the interface, the element mounted in the device can be moved in the axial direction against the force of a biasing spring during movement of the movable element and the accompanying approach of the conical surfaces, while its guiding support allows a movement which permits the centering surfaces to be brought into a joining position with centering surface axes aligned with each other free of constraint forces.

List of reference numerals

| | | | |
|---|---|---|---|
| 20 | dialysis machine | | |
| 22 | hinge connection | A22 | hinge axis |
| 24, 124 | front plate | | |
| 26 | accesses | A26 | access axis |
| 28 | base plate | | |
| 30, 130 | insert | | |
| 32 | insert wall | | |
| 34, 134 | quiver | A34, A134 | quiver axis |
| 36 | feed port | | |
| 38, 138 | discharge port | | |
| 40, 140 | bearing block | | |
| 42, 142 | centering surface | A42 | centering surface axis |
| 44 | bearing bore | | |
| 46 | biasing spring | | |
| 48, 148 | axial retaining ring | | |
| 50, 150 | centering surface | A50 | centering surface axis |
| 52 | annular groove | | |
| 54 | radial collar | | |
| 56, 156 | seal ring | | |
| 58 | plate | | |
| 60 | fastening bolt | | |
| 62 | bores | | |
| 64 | nut | | |
| 66 | plain bearing member | | |
| 68 | bearing bore | | |
| 144 | conical bearing surface | | |
| 170 | flute | | |

The invention claimed is:

1. An extracorporeal blood treatment device comprising at least one centering interface comprising:

a suction rod quiver comprising a first centering surface with a first centering surface axis;

a guiding support securing the suction rod quiver to a base, with the first centering surface being movable in an axial direction towards the guiding support against a bias of a biasing spring, and the suction rod quiver being angularly movable relative to the base; and a front plate movably guided relative to the guiding support between an open position and a closed position, the front plate comprising a second centering surface with a second centering surface axis;

wherein the suction rod quiver is movable in the axial direction against the bias of the biasing spring during a movement of the front plate from the open position to the closed position and an accompanying approach and contact of the first centering surface and the second centering surface, and the guiding support allows an angular movement of the suction rod quiver which permits the first centering surface and the second centering surface to move into a joining position with the first centering surface axis aligned with the second centering surface axis.

2. The extracorporeal blood treatment device according to claim 1, wherein the guiding support comprises a bearing block and plain bearing supported in the bearing block, and the suction rod quiver is supported to move in the axial direction in the plain bearing.

3. The extracorporeal blood treatment device according to claim 2, wherein the front plate is guided pivotally about an axis relative to the guiding support, and the bearing block is movable relative to the base at least in a plane that is perpendicular to the axis.

4. The extracorporeal blood treatment device according to claim 3, wherein the biasing spring bears against the bearing block.

5. The extracorporeal blood treatment device according to claim 2, wherein the plain bearing is supported in the bearing block via a spherical cap.

6. The extracorporeal blood treatment device according to claim 2, wherein the plain bearing has a conical bearing surface that extends and widens toward one end of the suction rod quiver.

7. The extracorporeal blood treatment device according to claim 1, wherein the first centering surface comprises an outer conical surface at an end face of the suction rod quiver, the second centering surface comprises an inner conical surface in the front plate, and the outer conical surface is engageable into a centering joint fitting engagement with the inner conical surface.

8. The extracorporeal blood treatment device according to claim 7, wherein at the suction rod quiver, the first centering surface adjoins a radial collar in which an annular seal is accommodated for contact with an inner wall of the front plate.

9. The extracorporeal blood treatment device according to claim 7, wherein a peripheral flute for receiving a seal ring is formed in the first centering surface.

10. The extracorporeal blood treatment device according to claim 7, wherein in the front plate, the second centering surface axis is tilted about an acute angle relative to a plane perpendicular to a movement axis of the front plate.

11. The extracorporeal blood treatment device according to claim 1, wherein an axis of the suction rod quiver is inclined relative to a horizontal plane at an angle up to 60°.

12. The extracorporeal blood treatment device according to claim 1, wherein the first centering surface and the second centering surface comprise respective conical surfaces.

13. The extracorporeal blood treatment device according to claim 1, wherein the front plate is attached to a housing of the extracorporeal blood treatment device via a hinge connection, and wherein the front plate accommodates an insert in which the first centering surface is formed.

14. The extracorporeal blood treatment device according to claim 13, wherein the at least one centering interface comprises:

a first centering interface having a first suction rod quiver and a respective second centering surface;

a second centering interface having a second suction rod quiver a respective second centering surface; and a shared or common bearing block adjacently supporting the first suction rod quiver and the second suction rod quiver;

wherein the insert comprises the respective second centering surface of the first centering interface and the respective second centering surface of the second centering interface, with the respective second centering surface of the first centering interface and the respective second centering surface of the second centering interface being adjacent horizontally or vertically in a plane perpendicular to a movement axis of the front plate.

15. A centering interface comprising:

a suction rod quiver comprising a first centering surface with a first centering surface axis;

a guiding support secured to a base with the first centering surface being movable in an axial direction towards the guiding support against a bias of a biasing spring, and the suction rod quiver being angularly movable relative to the base;

a front plate movably guided relative to the guiding support between an open position and a closed position, the front plate comprising a second centering surface with a second centering surface axis;

wherein the suction rod quiver is movable in the axial direction against the bias of the biasing spring during a movement of the front plate from the open position to the closed position and an accompanying approach and contact of the first centering surface and the second centering surface, and the guiding support allows an angular movement of the suction rod quiver which permits the first centering surface and the second centering surface to move into a joining position with the first centering surface axis aligned the second centering surface axis; and wherein the guiding support comprises a bearing block and plain bearing supported in the bearing block, and the suction rod quiver is supported to move in the axial direction in the plain bearing.

16. A centering interface comprising:

a suction rod quiver comprising a first centering surface with a first centering surface axis;

a guiding support securing the suction rod quiver to a base, with the first centering surface being movable in an axial direction towards the guiding support against a bias of a biasing spring, and the suction rod quiver being angularly movable relative to the base; and a front plate movably guided relative to the guiding support between an open position and a closed position, the front plate comprising a second centering surface with a second centering surface axis;

wherein the suction rod quiver is movable in the axial direction against the bias of the biasing spring during a movement of the front plate from the open position to the closed position and an accompanying approach and contact of the first centering surface and the second centering surface, and the guiding support allows an angular movement of the suction rod quiver which permits the first centering surface and the second centering surface to move into a joining position with the first centering surface axis aligned the second centering surface axis;

wherein the first centering surface comprises an outer conical surface at an end face of the suction rod quiver, the second centering surface comprises an inner conical surface in the front plate, and the outer conical surface is engageable into a centering joint fitting engagement with the inner conical surface; and wherein:

at the suction rod quiver, the first centering surface adjoins a radial collar in which an annular seal is accommodated for contact with an inner wall of the front plate; or a peripheral flute for receiving a seal ring is formed in the first centering surface.

* * * * *